US006383513B1

(12) United States Patent
Watts et al.

(10) Patent No.: US 6,383,513 B1
(45) Date of Patent: May 7, 2002

(54) COMPOSITIONS COMPRISING CANNABINOIDS

(75) Inventors: Peter James Watts; Stanley Stewart Davis, both of Nottingham (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/595,086

(22) Filed: Jun. 16, 2000

Related U.S. Application Data

(63) Continuation of application No. PCT/GB98/03703, filed on Dec. 10, 1998.

(30) Foreign Application Priority Data

Dec. 19, 1997 (GB) .............................................. 9726916

(51) Int. Cl.$^7$ .............................................. A61K 9/113
(52) U.S. Cl. ...................... 424/450; 424/455; 424/488; 424/489
(58) Field of Search .......................... 514/454; 424/450, 424/455, 489, 488

(56) References Cited

U.S. PATENT DOCUMENTS

| 4,464,378 | A | * | 8/1984 | Hussain ...................... 424/260 |
| 5,447,729 | A |   | 9/1995 | Belenduik et al. |
| 5,662,932 | A | * | 9/1997 | Amselem et al. ........... 424/450 |
| 5,804,592 | A | * | 9/1998 | Volicer ....................... 514/454 |
| 5,961,970 | A | * | 10/1999 | Lowell et al. ............. 424/93.1 |
| 5,989,535 | A | * | 11/1999 | Nayal ....................... 424/78.02 |
| 6,017,963 | A | * | 1/2000 | Alfonso et al. ............. 514/646 |
| 6,096,740 | A | * | 8/2000 | Mechoulam et al. .... 514/236.8 |

FOREIGN PATENT DOCUMENTS

| EP | 0 266 443 | 5/1988 |
| EP | 0 396 549 | 11/1990 |
| WO | 82 03768 | 11/1982 |
| WO | 97 11668 | 4/1997 |
| WO | 98 29096 | 7/1998 |

OTHER PUBLICATIONS

IDSON, Pharmaceutical Emulsions, in *Pharmaceutical Dosage Forms: Disperse Systems*, vol. 1, Marcel Dekker, Inc., New York, USA, pp. 199–243 (1988).

WADE, et al. Eds., *Handbook of Pharmaceutical Excipients*, 2d. Ed., American Pharmaceutical Assoc., Washington D.C., USA, pp. 352–354 (1994).

GURNY et al. Eds., *Bioadhesion –Possibilities and Future Trends*, Wissensschaftliche Verlagsgessellschant mbH, Stuttgart, Germany (1990).

LENAERTS et al. Eds., *Bioadhesive Drug Delivery Systems* (Too voluminous to include complete text) CRC Press, Inc., Boca Raton, Florida, USA (1990).

BARNES, Therapeutic Uses of Cannabinoids, *The Pharmaceutical Journal*, p. 104 (1997).

LITZINGER et al., Effect of Liposome Size on the Circulation Time and Intraorgan Distribution of Amphipathic Poly(ethylene glucol)–Containing Liposomes, *Biochemica et Biophysica Acta* 1190, pp. 99–107 (1994).

MARTYN et al. Nabilone in the Treatment of Multiple Sclerosis, *The Lancet*, vol. 345, p. 579 (1995).

BEAL et al., Dronabinol as a Treatment of Anorexia Associated with Weight Loss in Patients with Aids, *Journal of Pain and Symptom Management*, vol. 10, No. 2, pp. 89–97 (1995).

BURSTEIN et al., Synthetic Nonpsychotropic Cannabinoids with Potent Antiinflammatory, Analgesic, and Leukocyte Antiadhesion Activities, *J. Med Chem.*, vol. 35, pp. 3135–3141 (1992).

THOMPSON, Cyclodextrins–Enabling Excipients: Their Present and Future Use in Pharmaceuticals, *Critical Reviews™ in Therapeutic Drug Carrier Systems*, vol. 14, No. 1, pp. 1–104 (1997).

*The United States Pharmacopedia: The National Formulary*, United States Pharmacopedia Convention, Rockville, MD, USA (1995) (Too voluminous to include entire book).

* cited by examiner

Primary Examiner—James H. Reamer
(74) Attorney, Agent, or Firm—Akin, Gump, Strauss, Hauer & Feld, L.L.P.

(57) ABSTRACT

There is provided a composition for the nasal delivery of a cannabinoid which comprises a cannabinoid in a biphasic delivery system or a cannabinoid in a microsphere delivery system.

26 Claims, No Drawings

COMPOSITIONS COMPRISING CANNABINOIDS

CROSS REFERENCE TO RELATED APPLICATION

This application is a continuation of International Application PCT/GB98/03703, filed Dec. 10, 1998, the disclosure of which is incorporated herein by reference.

BACKGROUND OF THE INVENTION

This invention relates to pharmaceutical compositions for nasal delivery of cannabinoids and pharmaceutically acceptable salts and prodrugs thereof. The present invention also relates to the delivery of cannabinoids across the nasal mucosa of animals, especially humans, for the treatment of conditions such as pain, nausea and to stimulate appetite.

It is known that the active ingredients of cannabis, in the form of cannabinoids, can be useful in medical practice. The material delta-9-tetrahydrocannabinol (THC) is useful in the treatment of AIDS (J. Pain. Symptom Manage. 1995, 10, 89–97) when given orally. The drug is called Dronabinol and is formulated in sesame oil for oral delivery. The material is available commercially as the product Marinola® sold by Roxane in the USA.

Dronabinol (9-delta THC or THC) exhibits complex effects on the central nervous system (CNS), including central sympathomimetic activity. Dronabinol has been shown to have a marked appetite stimulant effect and has been used in the treatment of AIDS-related anorexia. Dronabinol also demonstrates effects on mood, cognition, memory and perception. Furthermore, the drug has anti-emetic properties and is used for the control of nausea and vomiting associated with cancer chemotherapy. These effects appear to be dose related. After oral administration, Dronabinol has an onset of action of approximately 0.5 to 1 hour and a peak effect at 2–4 hours. The duration of action for psychoactive effects is 4–6 hours, but the appetite stimulant effect may continue for 24 hours or longer after administration. Dronabinol is almost completely absorbed (90–95%) after single oral doses. However, due to a combined effect of first pass hepatic metabolism and high lipid solubility only 10–20% of the administered dose reaches the systemic circulation.

Studies on the use of THC in pain have been described in Pharm. J. 259, 104, 1997 and in Pharm. Sci. 3, 546, 1997. Nabilone, a synthetic cannabinoid has been reported to be an anti-emetic and anxiolytic, and also useful for treating pain of various etiologies such as multiple sclerosis (MS), peripheral neuropathy and spinal injuries (Lancet, 1995, 345, 579, Pharm. J. 259, 104, 1997). It is also known that inhaling cannabis by smoking can lead to a more rapid onset of action than oral ingestion.

A nasal formulation for the improved delivery of cannabinoids would be advantageous. Absorption of drugs from the nasal route tends to be rapid due to the large surface area available and the extensive blood supply. In addition, the drug is delivered directly to the systemic circulation and there is no loss due to "first pass" metabolism in the liver.

The nasal route is known to provide advantages for the delivery of drugs, and for some drugs the pharmacokinetic profile following nasal administration is similar to that found after intravenous administration. However, THC is in the form of an oily liquid which is highly lipid soluble and only sparingly soluble in water. Hence, the person skilled in the art would consider it impossible to produce a simple nasal solution or other simple gel or suspension formulation that could produce sufficient nasal absorption and therapeutic plasma levels.

The nasal administration of cannabinoids and their analogues has been described in U.S. Pat. No. 4,464,378. It was suggested that the drugs would be administered as simple nasal sprays, ointments, gels or suspensions, though no examples of formulations produced with THC were described. As explained above, the person skilled in the art would not expect such simple formulations of THC to be successful due to the low water solubility.

SUMMARY OF THE INVENTION

We have found surprisingly that cannabinoids and especially THC can be formulated successfully into a nasal product by using a biphasic delivery system and that such a biphasic delivery system provides improved nasal absorption and therapeutically relevant plasma levels. We have also found surprisingly that cannabinoids and especially THC can be delivered successfully via the nasal route by formulating into a microsphere system and particularly an albumin microsphere system.

According to a first aspect of the present invention there is provided a composition for the nasal delivery of a cannabinoid comprising a cannabinoid in a biphasic delivery system.

According to a second aspect of the present invention there is provided a composition for the nasal delivery of a cannabinoid comprising a cannabinoid in a microsphere delivery system.

By the term "cannabinoid" we include, inter alia, delta-8-tetrahydrocannabinol, delta-9-tetrahydrocannabinol, cannabidol, olivetol, cannabinol, cannabigerol, nabilone, delta-9-tetrahydro cannabinotic acid. The non-psychotropic cannabinoid 3-dimethylnepty 11 carboxylic acid homologine 8, delta-8-tetrahydrocannabinol, (J. Med. Chem. 35, 3135, 1992) as well as the prodrugs and pharmaceutically acceptable salts of cannabinoids are also suitable for the present invention and are included in the term "cannabinoid". A suitable prodrug is THC-hemisuccinate.

By a "biphasic delivery system" we are referring to a pharmaceutical composition comprising two phases of which one phase contains the dissolved, dispersed, solubilised or dissoluted drug and the other phase provides the carrier for the composition, for example the outer (surrounding) water phase in an emulsion system or the matrix of a microcapsule or microsphere system.

By "improved nasal absorption" we mean more than 10%, preferably more than 20% and most preferably more than 30% bioavailability of the drug after nasal administration. By the term bioavailability, we mean the absorption of the drug as measured by the area under the plasma level versus time profile following nasal administration as compared to the same parameter when the drug is given by intravenous injection; the values for the area being corrected for the dose of the drug if necessary.

DETAILED DESCRIPTION OF THE INVENTION

Biphasic delivery systems may be in the form of emulsion systems, such as an oil-in-water (O/W) emulsion, aqueous systems containing a solubilising or dispersing agent or microsphere systems where the phase containing the drug can be encapsulated by or dispersed on the surface of the microspheres.

An oil-in-water emulsion can be prepared using a combination of a pharmaceutically acceptable oil and emulsifier. The drug is dissolved in the oil phase which is then mixed with an aqueous phase typically containing a stabiliser under vigorous mixing, milling or homogenisation. Such emulsification methods are well described by Idson, Pharmaceutical Emulsions, Ch. 6, Pharmaceutical Dosage Forms, Disperse Systems. Vol. 1. Ed. Lieberman et al. Dekker, New York, 1988.

Preferred oils are vegetable oils such as soybean oil, olive oil, cotton seed oil, peanut oil, sesame oil and castor oil, with sesame oil and castor oil being preferred.

Vitamin E (tocopherol) can also be used as the oil phase. This material is also an antioxidant and can help to stabilise the chosen cannabinoid which tend to be prone to oxidation.

By the term Vitamin E (tocopherol) we include the $\alpha$-, $\beta$-, $\gamma$- and $\delta$-forms of tocopherol that differ by the number and position of methyl groups on the chromanol ring as well as the various isomers of these compounds. Pharmaceutically acceptable derivatives of tocopherol are also included, such as the esters of tocopherol, e.g. the linoleate, nicotinate, acetate or acid succinate ester.

The United States Pharmacopoeia describes Vitamin E as a form of $\alpha$-tocopherol. This includes d- or d, 1-$\alpha$-tocopherol, d- or d, 1-$\alpha$-tocopherol acetate and d- or d, 1-$\alpha$-tocopherol succinate. The term Vitamin E is also used as a generic description for all tocopherol and tocotrienol derivatives that exhibit Vitamin E activity. Thus, the term tocopherols is synonymous with Vitamin E, but also for methyl tocols.

A preferred Vitamin E composition for use in the emulsions of the present invention is $\alpha$-tocopherol as described in the United States Pharmacopoeia, Volume 23, 1995 which is also known as all-rac-$\alpha$-tocopherol. This material can be obtained from Roche Products Ltd., Heanor, UK.

The chosen emulsifier will be one that confers good stability to the emulsion and is pharmaceutically acceptable.

One preferred emulsifier is a block copolymer containing a polyoxyethylene block, i.e. a block made up of repeating ethylene oxide moieties. A suitable emulsifier of this type is Poloxamer, i.e. a polyoxyethylene-polyoxypropylene block copolymer, such as Poloxamer 188. See the Handbook of Pharmaceutical Excipients, p.352, 2nd Edn. Pharmaceutical Press, London, 1994, Eds, Wade and Weller.

Another preferred emulsifier is a phospholipid emulsifier. This can be any pharmaceutically acceptable material derived from soybeans or eggs, e.g. soy or egg lecithins. Egg lecithins, such as the material provided by Lipoid (Germany) known as Lipoid E80, which contains both phosphatidylcholine and phosphatidyl ethanoline, are preferred, although other phospholipid materials could be used including phospholipid-polyethylene glycol (PEG) conjugates (PEGylated phospholipids) that have been described for use in liposome systems, e.g. by Litzinger et al, Biochem Biophys Acta, 1190 (1994) 99–107.

The stability of the emulsion can be enhanced by the addition of a pharmaceutically acceptable co-emulsifier. Suitable co-emulsifiers include the fatty acids and salts thereof and bile acid and salts thereof. Suitable fatty acids are those having greater than 8 carbon atoms in their structure with oleic acid being a preferred material. A preferred bile acid is deoxycholic acid. Suitable salts are the pharmaceutically acceptable salts such as the alkali metal, e.g. Na and K, salts. These co-emulsifiers can be added at a concentration of 1% w/v, i.e. 1 g of co-emulsifier per 100 mls, or less of the total emulsion. Bile salts and oleic acid are preferred co-emulsifiers.

The quantity of oil in the emulsion can be from 5 to 50% on a v/v basis, preferably from 10 to 50% v/v and more preferably from 15 to 25% v/v. The drug is typically dissolved in the oil phase at a concentration of 0.1 to 20% w/v, preferably from 1 to 10% w/v, i.e. from 0.1 to 20, preferably from 1 to 10 g of drug in 100 ml of oil.

The emulsion formulation can be delivered to the nasal cavity using nasal spray devices known in the art such as those available from Pfeiffer and Valois. Such devices are familiar to the skilled artisan and can be single or multiple dosing systems.

The preferred volume for nasal administration is 150 $\mu$l (per nostril) containing a dose of about 1 mg of THC.

The biphasic delivery systems may also comprise a solubilising agent (solubilising phase) in an aqueous phase or in a solid phase. The solubilisation of the cannabinoid may be achieved by the use of a cyclodextrin or derivative thereof. Cyclodextrins are cyclic oligosaccharides which comprise glucopyranose units and cyclodextrins for use as pharmaceutical excipients have been described in detail by Thompson, Crit, Rev. Ther. Drug Carrier Sept. 14 1 (1997). Cyclodextrin and cyclodextrin derivatives which may be useful in the present invention include $\alpha$-cyclodextrin, $\beta$-cyclodextrin, $\gamma$-cyclodextrin, hydroxypropyl-$\beta$-cyclodextrin, dimethyl-$\beta$-cyclodextrin, sulphobutylether cyclodextrin, 2,6-dimethyl 14-$\beta$ cyclodextrin, 2,3,6-trimethyl 21-$\beta$ cyclodextrin.

The solubilising agent/cannabinoid formulation can be a simple aqueous product in which the drug is associated with the solubilising agent molecule, e.g. as a guest-host complex in which the drug (guest) is contained within a cavity in the solubilising agent molecule (host). Alternatively, the solubilising agent/cannabinoid formulation can be combined with the emulsion product described earlier when some of the drug can be present in the aqueous phase of the emulsion, solubilized in the solubilising agent, and a proportion of the drug can be present dissolved in the oil phase of the emulsion.

Alternatively, a guest-host product between a solubilising agent and a cannabinoid can be freeze dried to produce a powder material and then mixed with a bioadhesive microsphere such as a bioadhesive swelling starch microsphere as described in PCT/GB88/00836.

Other bioadhesive microspheres that may be used in the present compositions include those made from chitosan, polyvinyl pyrrolidone, alginate, polycarbophil, pectin, hyaluronic acid (and esters thereof), agar agarose, dextran, ovalbumin, collagen, casein.

By bioadhesion we mean a material that can interact with mucus or a mucosal surface and thereby provide retention of a drug at a mucosal surface for a period of time longer than that found for a simple liquid or powder system. The concept of bioadhesion has been well discussed in books and reviews such as Bioadhesive Drug Delivery Systems, Ed. Lenaerts and Gurney, CRC Press, Bala Raton, 1990 and Bioadhesion possibilities and future trends. Ed. Gurney and Junginger, Wissenschaftliche, Verlagsgellschaft mbh, Stuttgard, 1990.

Such a system will demonstrate good stability with high bioavailability when administered via the nasal route.

The weight ratio of solubilising agent to cannabinoid is typically in the range of from 100:1 to 5:1, preferably in the range of from 50:1 to 10:1 and more preferably in the range of from 30:1 to 10:1. The weight ratio of solubilising agent/cannabinoid guest-host product to carrier, e.g. water or microspheres, can be varied but is typically in the range of from 1:100 to 1:5, preferably in the range of from 1:50 to 1:10 and particularly in the range of from 1:25 to 1:15.

The systems containing a solubilising agent can also be mixed with a gelling system based on a polysaccharide such as gellan or pectin. These materials can be used to formulate a nasal liquid that can be sprayed into the nasal cavity but will then gel in the presence of endogenous cations. This gelling may prolong the contact time of the formulation in the nasal cavity either through bioadhesive interactions and/or the increase in viscosity. Pectin is a preferred material which can form gels in the presence of divalent cations such as calcium. Pectins with a low degree of esterification, i.e. less than 50%, for example, less than 35%, are suitable and these can be obtained from Copenhagen Pectin A/S as the commercial material known as Slendid Type 100 and Slendid Type 110. These pectins have been extracted from citrus peel and standardised by the addition of sucrose. The degree of esterification is less than 50% for both pectins and of the order of 10% for type 100 and 35% for type 110. Further suitable materials include GENU pectin types LM1912CS and Pomosin pectin types LM12CG and LM18CG. The concentration of pectin in the composition can be from 0.1% to 10% w/w, but is preferably from 0.5 to 5% w/w on the total weight of the composition.

The powdered product can be delivered nasally using an insufflator device of the type which is familiar to those skilled in the art. Such devices are manufactured by Teijin (Rhinocort™ insufflator), Bespak UK (nasal delivery device), Valois Monopoudre™, France.

A further embodiment of this invention is to incorporate a cannabinoid into a microsphere. It has been found that cannabinoids can be loaded into albumin microspheres and that it is possible to recover such microspheres in a dry powder for nasal administration. Other materials suitable for the preparation of microspheres include agar, alginate, chitosan, starch, hydroxyethyl starch, ovalbumin, agarose, dextran, hyaluronic acid, gelatin, collagen and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce a water in oil emulsion. Glutaraldehyde solution is then added to the emulsion and the emulsion stirred to cross-link the albumin. The microspheres can then be isolated by centrifugation, the oil removed and the spheres washed, e.g. with petroleum ether followed by ethanol. Finally, the microspheres can be sieved and collected and dried by filtration.

Starch microspheres can be prepared by adding a warm aqueous starch solution, e.g. of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurried in a solvent such as ethanol, after which the particles are again filtered off and laid to dry in air.

The microspheres can be hardened by well known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

Doses of the drug, e.g. THC, in the range 0.25 to 40 mg per day can be administered, a preferred range is 0.5 to 30 mg per day and a more preferred range 1 to 20 mg per day.

The present invention is now illustrated but not limited with reference to the following examples.

EXAMPLE 1

An Emulsion Formulation of THC Based on a Vegetable Oil

THC is dissolved in sesame oil to give a concentration of 35 mg/ml. Water containing the dispersed emulsifying agent Lipoid E80 at 1.5% w/v (i.e. 1.5 g of Lipoid E80 per 100 mls of water) is used as the continuous phase. The sesame oil-THC mixture is dispersed in the aqueous phase using a Silverson Mixer (Silverson Machine UN) in order to produce a course emulsion. The course emulsion is then passed through an APV. Lab 40 homogeniser to produce a fine emulsion of particles having an average size (i.e. diameter) of 250 nm as measured by Photon correlation spectroscopy. A small quantity, e.g. 1% w/w on the total weight of the oil phase, of tocopherol can be added to the oil phase to provide a stabilizing function. The total oil content of the final emulsion is 20% w/v, i.e. the emulsion contains 20 g of oil per 100 mls thereof. The emulsion formulation of THC could be delivered to the nasal cavity using known nasal spray devices. The preferred volume for nasal administration s 150 $\mu$l (per nostril) containing a dose of about 1 mg of THC.

EXAMPLE 2

Castor Oil Emulsion Formulation

The formulation is produced as described in Example 1 except the sesame oil phase is exchanged with castor oil. The particle size of the emulsion will be about 280 nm as measured by photon correlation spectroscopy.

EXAMPLE 3

Vitamin E Emulsion Formulation

The formulation is produced as described in Example 1 except the oil phase is exchanged with all-rac-$\alpha$-tocopherol (no additional antioxidant is then required) and sodium deoxycholate co-emulsifier is added to the aqueous phase containing the Lipoid E80 at a concentration of 1% w/v, i.e. 1 g of sodium deoxycholate per 100 mls of water.

EXAMPLE 4

Cyclodextrin/microsphere Formulation

Hydroxypropyl cyclodextrin is dissolved in water to a concentration of 100 mg/ml. THC is added to provide a concentration in the cyclodextrin solution of 10 mg/ml. The product is freeze-dried to produce a fluffy white powder. The freeze dried powder is mixed with starch microspheres (obtained from Perstorp, Sweden). The weight ratio of freeze-dried THC/cyclodextrin product to microspheres can be varied but a weight ratio of 1:1 is preferred. In order to obtain a dose of 1 mg of THC, 10 mg of the freeze dried product is mixed with 10 mg of the starch microspheres. The powdered product can be delivered using an insufflator device.

EXAMPLE 5

Albumin Microsphere Formulation

THC is dissolved in ethanol to provide a concentration of 100 mg/ml. The ethanolic solution of THC is then mixed slowly with human serum albumin (B.P) containing about 20% w/v, i.e. 20 g of albumin per 100 ml, of total protein to give a concentration of THC of 10 mg/ml in the albumin solution. The solution is then spray dried using a LabPlant spray drier at standard operating conditions. The resultant albumin microspheres are collected. These have an average size (i.e. diameter) of about 30 $\mu$m as measured using a Malvern Mastersizer apparatus. A dose of 20 mg of the powder could be administered nasally using an insufflator device familiar to the skilled artisan.

EXAMPLE 6

200 mg of THC dissolved in 2 ml of ethanol was added to 6 ml of sesame oil. The oil/ethanol/THC solution was stirred in an open vessel for 2 hours at 50–60° C. to evaporate the majority of the ethanol. Into 20 ml of 0.9% sodium chloride solution was dispersed 360 mg of egg yolk phospholipid (Lipoid E80) by warming to 40–50° C. The oil was added to the phospholipid dispersion and the two phases coarsely emulsified using an IKA laboratory homogeniser at 20,000 rpm for 2 minutes. This emulsion was then transferred to an APV Rannie Mini-Lab valve homogeniser and passed through twice at 500 bar to produce a milky off-white product. The final product contained 6.7 mg/ml THC. A nasal administration of 150 $\mu$l of the emulsion would provide 1 mg of THC.

EXAMPLE 7

1 g of cross-linked starch micro spheres (Eldexomer™, Perstorp Pharma, Sweden) were weighed into a glass vial. 1 ml of 25 mg/ml THC in ethanol was added to the starch microspheres. The vial containing microspheres suspended in THC solution was transferred to a water bath at 70° C. to evaporate the ethanol. After 3 hours, the majority of the ethanol had evaporated. The product was transferred from the vial into a small tray and dried in an oven at 60° C. for 1 hour. The lightly aggregated microspheres were broken up using a spatula to form a free-flowing powder. 41 mg of powder contained a 1 mg dose of THC.

EXAMPLE 8

1 g of human serum albumin (Sigma) was dissolved in 50 ml of water. 2 ml of 25 mg/ml THC in ethanol was added to the albumin solution to form a cloudy dispersion. The dispersion was processed using a LabPlant SD-05 spray drier (175° C. inlet temperature, 0.1 mm nozzle diameter, airflow 20–22 'units', atomising pressure 1.8 bar, pump speed 10 ml/min). The result was 0.33 grams of powder (31% yield) which had a particle size (determined using light microscopy) in the range 1–10 $\mu$m.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A composition for nasal delivery comprising a cannabinoid in a biphasic delivery system, wherein the biphasic delivery system is an oil-in-water emulsion.
2. A composition according to claim 1, wherein the oil phase in the emulsion system is a vegetable oil.
3. A composition according to claim 2, wherein the oil phase in the emulsion system is castor oil.
4. A composition according to claim 1, wherein the oil phase in the emulsion system is tocopherol.
5. A composition according to claim 1, wherein the emulsifier is a phospholipid.
6. A composition according to claim 1, wherein the emulsifier is a block copolymer.
7. A composition according to claim 1, further comprising a solubilising agent for the cannabinoid.
8. A composition according to claim 7, wherein the solubilising agent is a cyclodextrin or a derivative thereof.
9. A composition according to claim 7, further comprising a polysaccharide gelling system.
10. A composition according to claim 9, wherein the polysaccharide is a pectin.
11. A composition for nasal delivery comprising a cannabinoid in a microsphere delivery system.
12. A composition according to claim 11, wherein the microsphere delivery system is a biphasic system comprising a material accommodating the cannabinoid which is encapsulated by or dispersed on the surface of a microsphere carrier matrix.
13. A composition according to claim 12, wherein the material accommodating the cannabinoid is a solubilising agent which forms a guest-host product with the cannabinoid.
14. A composition according to claim 13, wherein the solubilising agent is a cyclodextrin or a derivative thereof.
15. A composition according to claim 11, wherein the microspheres are made of albumin.
16. A composition according to claim 15, wherein the selected albumin microspheres are produced by a process of spray drying.
17. A composition according to claim 11, wherein the microspheres are starch microspheres.
18. A composition according to claim 17, wherein the starch microspheres are cross-linked.
19. A composition according to claim 1, wherein the cannabinoid is dronabinol.
20. A method for the treatment of pain, nausea or appetite loss which comprises administration of a composition according to claim 1 to a patient in need of such treatment.
21. The use of a cannabinoid in the manufacture of a composition according to claim 1, for treating a patient in need of a cannabinoid.
22. The use of a cannabinoid in the manufacture of a composition according to claim 1, for treating pain or nausea or to stimulate appetite.
23. The use of a composition according to claim 1, for the manufacture of a medicament for treating a patient in need of a cannabinoid.
24. The use of a composition according to claim 1, for the manufacture of a medicament for treating pain or nausea or to stimulate appetite.
25. The use of a cannabinoid in the manufacture of a composition according to claim 1, for nasal delivery.
26. The use of a composition according to claim 1, for the manufacture of a medicament for nasal delivery.

* * * * *